United States Patent

Yamada et al.

(10) Patent No.: US 9,459,214 B2
(45) Date of Patent: Oct. 4, 2016

(54) SENSOR UNIT ARRAY, RAMAN SPECTROSCOPIC DEVICE, AND ELECTRONIC APPARATUS

(71) Applicant: Seiko Epson Corporation, Tokyo (JP)

(72) Inventors: Kohei Yamada, Suwa (JP); Akiko Yamada, Suwa (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 14/603,711

(22) Filed: Jan. 23, 2015

(65) Prior Publication Data

US 2015/0211930 A1    Jul. 30, 2015

(30) Foreign Application Priority Data

Jan. 27, 2014   (JP) .................................. 2014-012556

(51) Int. Cl.
*G01J 3/44* (2006.01)
*G01N 21/65* (2006.01)

(52) U.S. Cl.
CPC .............. *G01N 21/658* (2013.01); *G01J 3/44* (2013.01)

(58) Field of Classification Search
CPC ........ G01J 3/44; G01J 3/4412; G01J 3/0202; G01J 3/0264; G01J 21/658
USPC .......................... 356/244, 246, 301, 319, 326
See application file for complete search history.

(56) References Cited

U.S. PATENT DOCUMENTS

| | | | |
|---|---|---|---|
| 5,999,255 A * | 12/1999 | Dupee | G01J 3/02 356/301 |
| 6,864,984 B2 | 3/2005 | Naya et al. | |
| 7,009,706 B2 | 3/2006 | Mori et al. | |
| 7,030,988 B2 | 4/2006 | Kubo et al. | |
| 8,531,661 B2 | 9/2013 | Sakagami et al. | |
| 2002/0149775 A1* | 10/2002 | Mori | G01N 21/553 356/445 |
| 2008/0239307 A1* | 10/2008 | Talley | G01J 3/02 356/301 |
| 2014/0168727 A1* | 6/2014 | Kawamura | H04N 1/19 358/482 |

FOREIGN PATENT DOCUMENTS

| | | |
|---|---|---|
| JP | 2001-330560 A | 11/2001 |
| JP | 2002-277390 A | 9/2002 |
| JP | 2003-139687 A | 5/2003 |
| JP | 2003-240705 A | 8/2003 |
| JP | 2004-053279 A | 2/2004 |
| JP | 2009-162637 A | 7/2009 |
| JP | 2012-063155 A | 3/2012 |

\* cited by examiner

*Primary Examiner* — Hoa Pham
(74) *Attorney, Agent, or Firm* — Harness, Dickey & Pierce, P.L.C.

(57) ABSTRACT

A sensor unit array includes a first sensor unit and a second sensor unit. The first sensor unit and the second sensor unit each include a sensor chip and a holding body adapted to hold the sensor chip. A housing chamber is formed by a holding body of the first sensor unit and a holding body of the second sensor unit when the first sensor unit and the second sensor unit are disposed adjacent to each other. The sensor chip of one of the first sensor unit and the second sensor unit is disposed in the housing chamber.

17 Claims, 6 Drawing Sheets

FIG. 10

SENSOR UNIT ARRAY, RAMAN SPECTROSCOPIC DEVICE, AND ELECTRONIC APPARATUS

BACKGROUND

1. Technical Field

The present invention relates to a sensor unit array, a Raman spectroscopic device, and an electronic apparatus.

2. Related Art

In recent years, surface enhanced Raman Scattering (SERS) using a localized surface plasmon resonance (LSPR) has attracted attention as a spectroscopic technology for detecting low-concentration target molecules at high sensitivity. The SERS is a phenomenon in which an enhanced electric field is formed on a metal surface having nanometer-scale structures, and the Raman scattering light is enhanced by $10^2$ through $10^{14}$ times by the enhanced electric field. When excitation light such as a laser beam is applied in the state in which a substance to be the target is adsorbed on such a metal surface as described above, light (Raman scattering light) having a wavelength slightly shifted from the wavelength of the excitation light is scattered as much as the vibration energy of the substance (molecules). By performing a spectroscopic process on the scattering light, a spectrum (fingerprint spectrum) specific to the type (molecular species) of the substance can be obtained. By using the SERS, the position and the shape of the fingerprint spectrum can be analyzed at high sensitivity, and it becomes possible to qualitatively and quantitatively detect the substance at extremely high sensitivity.

The sensor having such a metal surface can provide highly sensitive measurement, and can be extremely miniaturized at the same time. However, the easiness of handling by the user is impaired by miniaturizing the sensor in some cases, and JP-A-2001-330560, for example, discloses an attempt to enhance the handling easiness by putting a plurality of measuring chips in a housing called cassette.

In general, in the chips used for the SERS, the measurement is performed by collecting a laser beam to have a spot of several micrometers through several hundred micrometers with a lens with respect to a structure having arranged nanoparticles of noble metal such as gold or silver. Therefore, if the chip is used as a sensor chip, it is sufficient for the chip to have a planar size of about 3 mm on a side.

Further, in particular in the purpose of taking and then analyzing a biological gas such as an exhaled gas or a skin gas, the chip is always exposed to a high-humidity environment. In this case, even if the contact of the moisture with the chip is reduced using a moisture removing filter or the like, a small amount of water molecules continues to be adsorbed on the metal surface of the chip. Therefore, the entire metal surface is covered with the water molecules if it is used for several days, for example, and the adsorption of the target molecules is hindered in some cases. Therefore, under such circumstances, it is necessary to replace the sensor chip at a higher frequency.

Therefore, in order to realize the detection device which is small in size and high in sensitivity, and can easily be used by the user at any location, it is necessary to make it easy to replace such a small sensor chip.

JP-A-2001-330560 described above fails to disclose anything about storage, deterioration, and so on of the chips although there is a description that the chips are housed in the cassette to enhance the handling easiness. Further, since it results that a separate configuration such as the cassette from the chips is added, it cannot necessarily be said that both of the miniaturization and the handling easiness are sufficiently achieved.

SUMMARY

An advantage of some aspects of the invention is to provide a sensor unit array that is small in size and easy to handle, and a Raman spectroscopic device or an electronic apparatus using the sensor unit array.

The invention can be implemented as the following aspects or application examples.

A sensor unit array according to an aspect of the invention includes a first sensor unit, and a second sensor unit, wherein the first sensor unit and the second sensor unit each include a sensor chip and a holding body adapted to hold the sensor chip, a housing chamber partitioned by a holding body of the first sensor unit and a holding body of the second sensor unit is formed when the first sensor unit and the second sensor unit are disposed adjacently to each other, and the sensor chip of either one of the first sensor unit and the second sensor unit is disposed in the housing chamber.

In such a sensor unit array, plural sensor units are arranged adjacently to each other, and thus, even if the size of each of the sensor units is small, the size easy to handle with a hand of the user is achieved. Further, since the sensor chip is protected from disturbances such as contact in handling by the user, keeping, and storing the sensor chip, the characteristic of high sensitivity can be maintained.

In the sensor unit array according to the aspect of the invention, the holding body may include a base section and a cylindrical section disposed so as to be connected to the base section, the sensor chip may be provided to the base section, and the sensor chip of the first sensor unit may be housed in the housing chamber when the housing chamber is formed with the base section of the first sensor unit, the base section and the cylindrical section of the second sensor unit.

Since in such a sensor unit array, the sensor chip is provided to the base section of the holding body, when the first sensor unit is separated from the second sensor unit, and the housing chamber is opened, the sensor chip is disposed in an end portion of the sensor unit. Therefore, a member of the sensor unit for shielding the sensor chip from the lateral side does not exist, and it is easy for the fluid including the target substance to have contact with the sensor chip from the lateral side. Therefore, the measurement with higher sensitivity is achievable.

In the sensor unit array according to the aspect of the invention, the base section of the first sensor unit may engage with an inner surface of the cylindrical section of the second sensor unit when the first sensor unit and the second sensor unit are disposed adjacently to each other.

In such a sensor unit array, the shape of the housing chamber can be maintained with an appropriate strength, and further, it is easy to separate the first sensor unit and the second sensor unit from each other with a hand of the user.

In the sensor unit array according to the aspect of the invention, the base section of the first sensor unit may be bonded to an inner surface of the cylindrical section of the second sensor unit when the first sensor unit and the second sensor unit are disposed adjacently to each other.

In such a sensor unit array, the shape of the housing chamber can be maintained with an appropriate strength, and further, it is easy to separate the first sensor unit and the second sensor unit from each other with a hand of the user.

In the sensor unit array according to the aspect of the invention, the holding body may include a rotation restricting mechanism adapted to restrict the first sensor unit and the second sensor unit from rotating relatively to each other around an axis along a direction in which the first sensor unit and the second sensor unit are arranged when the first sensor unit and the second sensor unit are adjacent to each other.

According to such a sensor unit array, the angles of the respective sensor chips of the first sensor unit and the second sensor unit around the axis along the direction, in which the first sensor unit and the second sensor unit are arranged, can be made uniform. Thus, in the case of, for example, mounting the sensor unit array to the Raman spectroscopic device, the incident angle of the excitation light from the light source with respect to the sensor chip, and the rotational angle of the sensor chip with respect to the light source can be stably set to the predetermined angles in each of the sensor units. In the case in which, for example, the excitation light is polarized light, and the sensor chip has an anisotropic arrangement of the metal particles, an appropriate arrangement can be obtained. Thus, in the case of mounting such a sensor unit array to the Raman spectroscopic device, the operation for appropriately mounting the sensor unit array becomes extremely easy, and it is possible to further simplify the handling.

In the sensor unit array according to the aspect of the invention, the base section of the first sensor unit may be screwed together with an inner surface of the cylindrical section of the second sensor unit when the first sensor unit and the second sensor unit are disposed adjacently to each other.

In such a sensor unit array, the shape of the housing chamber can be maintained with an appropriate strength, and further, it is easy to separate the first sensor unit and the second sensor unit from each other with a hand of the user.

In the sensor unit array according to the aspect of the invention, an inert gas may be encapsulated in the housing chamber.

Adsorption of the target molecules is hindered due to the noise molecules such as water molecules adsorbed to the sensor chip during transportation and keeping, and thus, the characteristic of the sensor chip is apt to be deteriorated. Therefore, it is preferable to airtightly encapsulate the unused sensor chips in a state maintained in low humidity. According to such a sensor unit array, the inert gas is encapsulated in the housing chamber, the deterioration of the sensor chip is suppressed in keeping and storing the sensor unit array, and thus, the characteristic of high sensitivity can be maintained for a longer period of time.

A sensor unit array according to another aspect of the invention includes a first sensor unit, and a second sensor unit, wherein the first sensor unit and the second sensor unit each include a base body, and a sensor section provided to the base body, a housing chamber partitioned by the respective base bodies of the first sensor unit and the second sensor unit is formed when the first sensor unit and the second sensor unit are disposed adjacently to each other, and the sensor section of either one of the first sensor unit and the second sensor unit is disposed in the housing chamber.

In such a sensor unit array, plural sensor units are arranged adjacently to each other, and thus, even if the size of each of the sensor units is small, the size easy to handle with a hand of the user is achieved. Further, since in such a sensor unit array, the sensor section is disposed inside the housing chamber, when keeping or storing the sensor unit array, deterioration of the sensor section is inhibited, and thus, the characteristic of high sensitivity can be maintained.

Further, since the sensor section can be protected from disturbances such as contact in handling by the user, keeping, and storing the sensor section, the characteristic of high sensitivity can be maintained.

A Raman spectroscopic device according to still another aspect of the invention includes a mounting section adapted to mount the sensor unit array described above, a light source adapted to irradiate the sensor unit array with excitation light, and a detector adapted to detect light emitted from the sensor unit array.

According to such a Raman spectroscopic device, since the sensor unit array described above is mounted, the handling of the device is easy. Further, since the sensor chip is disposed inside the housing chamber, the sensor chip can be easily replaced.

An electronic apparatus according to yet another aspect of the invention includes the Raman spectroscopic device described above, an operation section adapted to perform an operation on health medical information based on detection information from the detector, a storage section adapted to store the health medical information, and a display section adapted to display the health medical information.

According to such an electronic apparatus, the detection of a trace substance can be easily achieved, and thus, the accurate health medical information can be provided.

BRIEF DESCRIPTION OF THE DRAWINGS

Embodiments of the invention will be described with reference to the accompanying drawings, wherein like numbers reference like elements.

FIGS. 4A-1, 4A-2, 4B-1, and 4B-2 are schematic diagrams of planar views and cross-sectional views of the sensor chip according to the embodiment.

DESCRIPTION OF EXEMPLARY EMBODIMENTS

Hereinafter, some embodiments of the invention will be explained. The embodiments explained hereinafter are each for explaining an example of the invention. The invention is not at all limited by the embodiments described below, and includes a variety of types of modified configurations to be put into practice within the scope or the spirit of the invention. It should be noted that all of the constituents explained hereinafter are not necessarily essential elements of the invention.

1. Sensor Unit Array

Figure 1A:
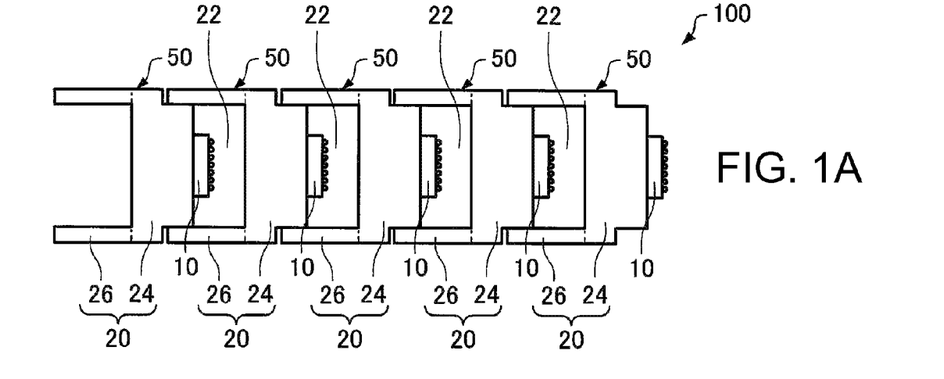
FIGS. 1A and 1B are each a schematic diagram of a cross-section of a sensor unit array according to an embodiment of the invention.
Figure 1B:
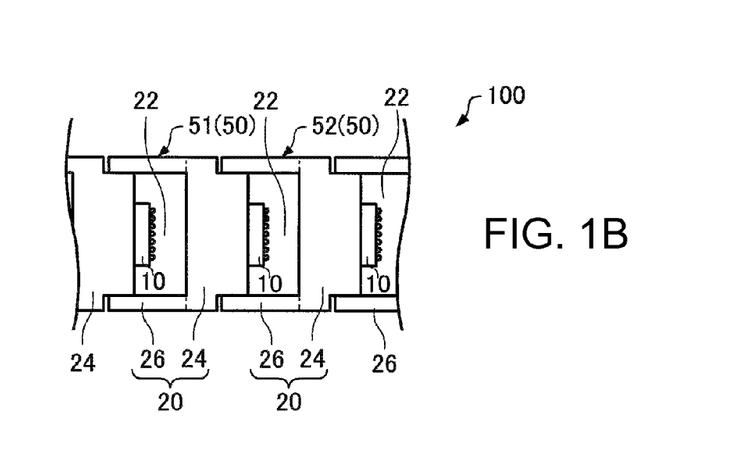
Figure 2A:
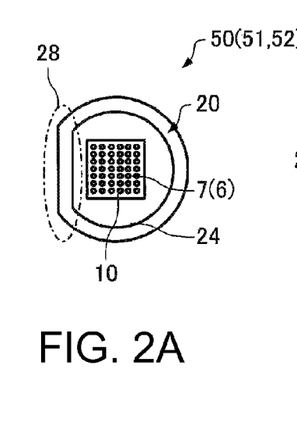
FIGS. 2A through 2C are appearance diagrams schematically showing a sensor unit according to the embodiment.
Figure 2B:
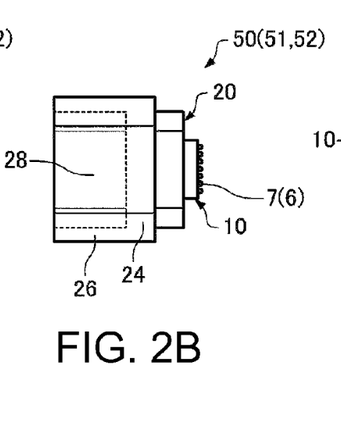
Figure 2C:
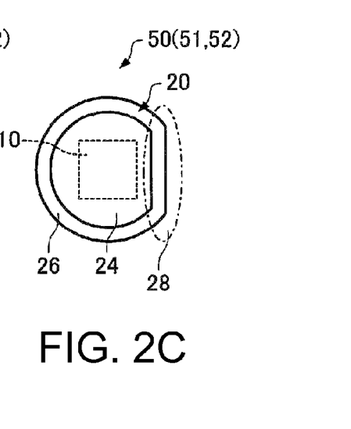

FIGS. 1A and 1B are each a schematic diagram of a cross-section of a sensor unit array 100 according to the present embodiment. FIGS. 2A through 2C are appearance diagrams of a sensor unit 50 according to the present embodiment viewed from three directions, respectively.

The sensor unit array 100 according to the present embodiment includes a plurality of sensor units 50. The sensor unit array 100 according to the present embodiment has the plurality of sensor units 50 arranged so as to be adjacent to each other. In other words, the sensor unit array 100 according to the present embodiment has a first sensor unit 51 and a second sensor unit 52 arranged so as to be adjacent to each other.

Since the number of sensor units 50 provided to the sensor unit array 100 according to the present embodiment is not limited providing the number is plural, in the present embodiment, as shown in FIG. 1B, the two sensor units 50 out of the plurality of sensor units 50 of the sensor unit array 100 are provided with ordinal numbers and reference numerals as the "first sensor unit 51" and the "second sensor unit 52" in some cases for the sake of convenience of explanation. It should be noted that in the case of providing such ordinal numbers, the two sensor units 50 can be arbitrarily selected from the sensor unit array 100, and irrespective of which sensor units 50 are selected, the both sensor units 50 can be located adjacent to each other, and the explanation regarding each of the sensor units 51, 52 is substantially the same as the explanation regarding the sensor units 50.

1.1. Sensor Unit

The sensor unit 50 of the present embodiment includes a sensor chip 10 and a holding body 20. The plurality of sensor units 50 can include the respective sensor chips 10 that are different in structure from each other, or can include the respective sensor chips 10 having respective structures that are the same as each other. Further, the plurality of sensor units 50 can include the respective holding bodies 20 that are different in structure from each other, or can include the respective holding bodies 20 having respective structures that are the same as each other.

1.1.1. Sensor Chip

The sensor chip is not particularly limited as long as the sensor chip can generate the surface plasmon resonance (SPR) on the surface to which the target substance is adsorbed, and which is irradiated with the excitation light. As an example of such a surface, there can be cited a configuration which is a surface having metal nanoparticles arranged randomly or regularly, and on which the light (the Raman scattering light) with a wavelength shifted from the wavelength of the excitation light is scattered as much as the vibration energy of the target substance when being irradiated with the excitation light in the state in which the target substance is adsorbed on the surface. Such scattering is the surface enhanced Raman scattering (SERS), and the Raman scattering light is enhanced to be $10^2$ through $10^{14}$ times. Further, by performing a spectroscopic process on the SERS light, a spectrum (fingerprint spectrum) specific to the type (molecular species) of the target substance can be obtained at high sensitivity.

Figure 3:
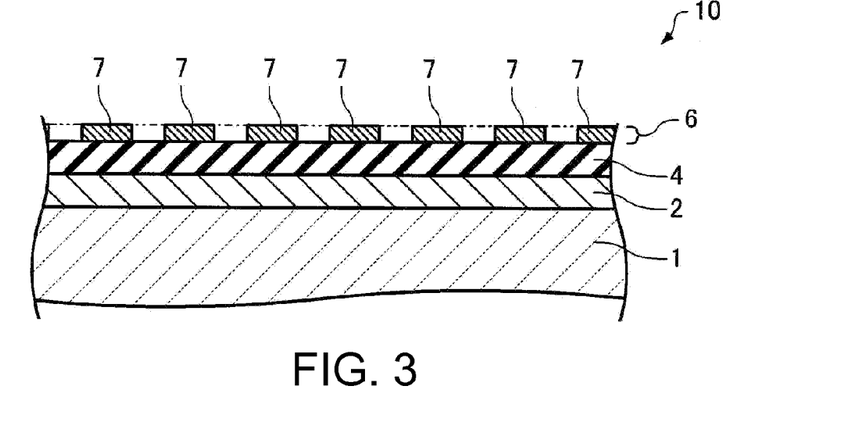
FIG. 3 is a cross-sectional view of a sensor chip according to the embodiment.
Figure 4A:
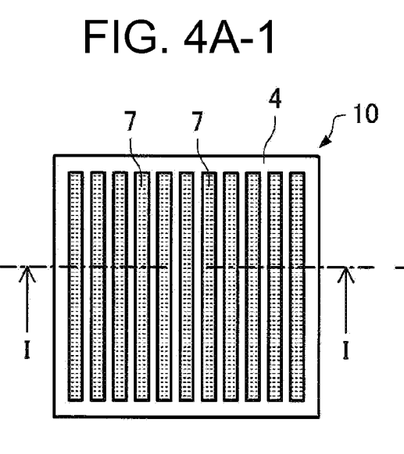
Figure 4A:
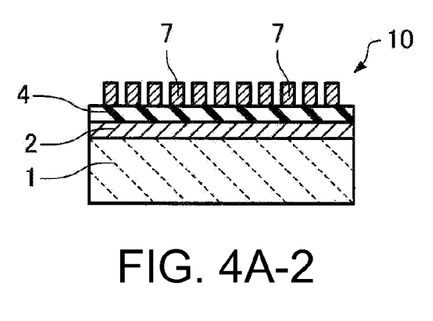
Figure 4B:
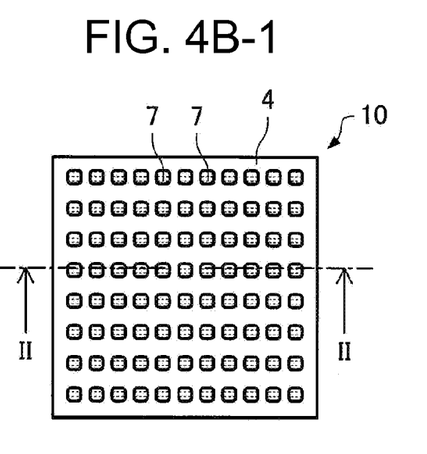
Figure 4B:
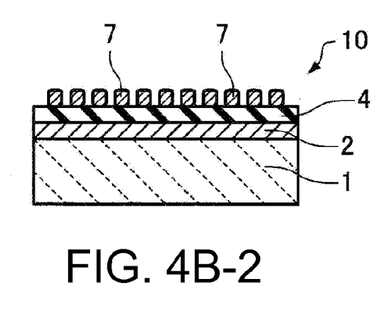

Hereinafter, the sensor chip 10 having the metal particles as an example of metal fine structures 7 arranged on a surface will be explained as an embodiment of the sensor chip. FIG. 3 is a schematic diagram of a cross-section of the sensor chip 10. FIGS. 4A-1, 4A-2, 4B-1, and 4B-2 are diagrams of two configurations of the sensor chip 10 viewed in a planar manner (viewed from the thickness direction of a metal layer 2) and cross-sectional views thereof. The cross-section along the I-I line shown in FIG. 4A-1 corresponds to FIG. 4A-2, and the cross-section along the II-II line shown in FIG. 4B-1 corresponds to FIG. 4B-2, respectively. The sensor unit 10 of the present embodiment includes a metal layer 2, a dielectric layer 4, and a metal fine structure layer 6.

1.1.1.1. Metal Layer

The sensor chip 10 of the present embodiment includes the metal layer 2. The metal layer 2 is not particularly limited providing the metal layer provides a metal surface, which does not transmit light, and can have a shape of, for example, a film, a plate, a layer, or a membrane. The metal layer 2 can also be disposed above, for example, a substrate 1. The substrate 1 in this case is not particularly limited, but one difficult to affect a propagating surface plasmon to be excited in the metal layer 2 is preferable. As the substrate 1, there can be cited, for example, a glass substrate, a silicon substrate, and a resin substrate. The shape of the surface of the substrate 1 on which the metal layer 2 is disposed is not particularly limited. In the case of forming a predetermined structure on the surface of the metal layer 2, it is possible to provide a surface corresponding to the predetermined structure. Further, in the case of making the surface of the metal layer 2 flat, it is possible to make the surface of the corresponding part flat. In the example shown in FIG. 3, the metal layer 2 having a layered shape is disposed above the surface (flat surface) of the substrate 1.

In the present specification, in the sensor chip 10, the thickness direction of the metal layer 2 is referred to as a thickness direction, a height direction, and so on in some cases. In the present embodiment, the thickness direction of the metal layer 2 coincides with a thickness direction of the dielectric layer 4 and the metal fine structure layer 6. Further, in the case in which the metal layer 2 is disposed on the surface of the substrate 1, the normal direction of the surface of the substrate 1 is referred to as the thickness direction or the height direction in some cases. Further, in some cases, a direction toward the metal layer 2 viewed from the substrate 1 is expressed as top or upside, and the opposite direction is expressed as bottom or downside.

Further, in the present specification, the expression of, for example, "a member B is disposed above a member A" has a meaning including the case in which the member B is disposed so as to have contact with an upper surface of the member A, and the case in which the member B is disposed above the member A via another member or a space.

The metal layer 2 can be formed by a process such as a vapor deposition process, a sputtering process, a casting process, or a machining process. In the case in which the metal layer 2 is disposed above the substrate 1 as a thin film, it is also possible to dispose the metal layer above the entire surface of the substrate 1, or above a part of the substrate 1. The thickness of the metal layer 2 is not particularly limited, and can be set to be, for example, no smaller than 10 nm and no larger than 1 mm, preferably no smaller than 20 nm and no larger than 100 μm, and more preferably no smaller than 30 nm and no larger than 1 μm.

The metal layer 2 is preferably formed of metal in which there can exist an electric field where an electric field provided by the incident light (the excitation light) and polarization induced by the electric field vibrate in respective phases opposite to each other, namely metal in which the real part of the dielectric function can have a negative value (a negative dielectric constant) and the dielectric constant in the imaginary part can be smaller than an absolute value of the dielectric constant in the real part in the case in which a specific electric field is applied. As examples of the metal capable of having such a dielectric constant in the visible range, there can be cited silver, gold, aluminum, copper, platinum, alloys of any of these metals, and so on. Further, the surface (the end surface in the thickness direction) of the metal layer 2 can, but is not required to, be a specific crystal plane. Further, the metal layer 2 can be formed extending to the outside of the dielectric layer 4 in the planar view.

The metal layer 2 can have a function of generating a propagating surface plasmon (PSP) in the sensor chip 10. Under a specific condition, by the light entering the metal layer 2, the propagating surface plasmon occurs in the vicinity of the surface (the end surface in the thickness direction) of the metal layer 2. In the present specification, a quantum of the vibration formed of the vibration of the charges in the vicinity of the surface of the metal layer 2 and the electromagnetic wave combined with each other is referred to as a surface plasmon polariton (SPP) in some cases. In the case of generating the propagating surface plasmon on such a metal layer 2, it is also possible to make the propagating surface plasmon interact with a localized surface plasmon (LSP) generating on the metal fine structure layer 6 described later.

1.1.1.2. Dielectric Layer

The sensor chip 10 according to the present embodiment includes the dielectric layer 4 for electrically separating the metal layer 2 and the metal fine structure layer 6 (the metal fine structures 7) from each other. As shown in FIG. 3, the dielectric layer 4 is disposed above the metal layer 2. Thus, the metal layer 2 and the metal fine structures 7 included in the metal fine structure layer 6 can be separated from each other. The dielectric layer 4 can have a shape of a film, a layer or a membrane.

The dielectric layer 4 is only required to have a positive dielectric constant, and can be formed of, for example, $SiO_2$, $Al_2O_3$, $TiO_2$, a polymer, or indium tin oxide (ITO). Further, the dielectric layer 4 can be formed of a plurality of layers having different materials from each other. Among these materials, $SiO_2$ is more preferable as the material of the dielectric layer 4. According to this configuration, in measuring the sample using the incident light (the excitation light) having a wavelength equal to or longer than 400 nm, it is possible to make it easy to enhance both of the incident light (the excitation light) and the Raman scattering light.

The thickness of the dielectric layer 4 is designed considering the wavelength and so on of the Raman scattering light when inputting the incident light (the excitation light) having a specific wavelength, with which the sensor chip 10 is irradiated. The dielectric layer 4 can be formed by a process such as a vapor deposition process, a sputtering process, a CVD process, or a variety of types of coating processes. The dielectric layer 4 can be disposed above the entire surface of the metal layer 2, or can be disposed above a part of the surface of the metal layer 2. The dielectric layer 4 is disposed below at least the metal fine structure layer 6, and can also be disposed at a position where the metal fine structure layer 6 does not exist.

The thickness of the dielectric layer 4 is not particularly limited, and can be set to be, for example, no smaller than 10 nm and no larger than 2000 nm, preferably no smaller than 20 nm and no larger than 500 nm, and more preferably no smaller than 20 nm and no larger than 300 nm. The light can be propagated in the dielectric layer 4 (in the planar direction, namely the direction parallel to the dielectric layer 4). Further, the dielectric layer 4 can propagate the propagating surface plasmon (PSP) generated in the vicinity of the interface between the dielectric layer 4 and the metal layer 2 in the dielectric layer 4 (in the planar direction). Further, in the case of assuming the metal fine structure layer 6 as one layer, the configuration can be assumed as a resonator having a structure in which the light is reflected by the metal layer 2 and the metal fine structure layer 6 at both ends, and the dielectric layer 4 can function as a light path of the resonator. In such a resonator, superposition between the incident light (the excitation light) and the reflected light can be caused. By setting the thickness of the dielectric layer 4 so that an antinode of the standing wave caused by the superposition between the incident light (the excitation light) and the reflected light is located in the vicinity of the center in the thickness direction of the metal fine structure layer 6, the intensity of the LSP caused on the metal fine structure layer 6 can be further enhanced. It is also possible to set the thickness of the dielectric layer 4 taking such a point into consideration, and in this case, it is possible to cite an example of setting the thickness of the dielectric layer 4 to 230 nm in the case in which the wavelength of the incident light (the excitation light) is 633 nm, but the thickness of the dielectric layer 4 is not limited to this example.

1.1.1.3. Metal Fine Structure Layer

The metal fine structure layer 6 is disposed above the dielectric layer 4. In the planar view, the metal fine structure layer 6 is formed in a part or the whole of the area where the dielectric layer 4 is formed. The metal fine structure layer 6 includes the metal fine structures 7. Although the metal fine structures 7 each have a particulate structure (a metal particle) in the example shown in the drawing, the metal fine structures 7 are not limited to such a configuration. The number, the size (dimension), the shape, the arrangement, and so on of the metal fine structures 7 included in the metal fine structure layer 6 are not particularly limited. Further, the metal fine structure layer 6 can also include a gas (a space), a dielectric material, and so on besides the metal fine structures 7.

The metal fine structure layer 6 is defined as a part between the upper surface of the dielectric layer 4 and a plane having contact with the upper end of the metal fine structures 7 on the side separate from the dielectric layer 4. For example, it is assumed that in the case in which the metal fine structure layer 6 includes the metal fine structures 7 and a gas (a space), the upper surface and the lower surface of the metal fine structure layer 6 become imaginary planes, and the gas (the space) disposed on the lateral side of each of the metal fine structures 7 is also included in the metal fine structure layer 6.

The planar shape of the metal fine structure layer 6 is not particularly limited, and it is possible to adopt an arbitrary shape such as a rectangular shape, a polygonal shape, a circular shape, or an elliptical shape. Further, by adopting a shape similar to the shape of the irradiation area with the incident light (the excitation light) as the planar shape of the metal fine structure layer 6, the energy of the incident light (the excitation light) can be more efficiently used for the electrical field enhancement in some cases.

The number, the size (dimension), the shape, the arrangement, and so on of the metal fine structures 7 included in the metal fine structure layer 6 are not particularly limited providing the metal fine structures 7 can generate the localized surface plasmon due to the irradiation with the incident light (the excitation light). FIG. 3 shows an example of the metal fine structures 7 included in the metal fine structure layer 6 as particulate fine structures (metal particles). Further, in the example shown in FIGS. 4A-1, 4A-2, the metal fine structure layer 6 has a stripe shape having a plurality of metal fine structures 7 arranged side by side at a predetermined pitch in a predetermined direction in a planar view. In other words, in this example, the metal fine structure layer 6 has the metal fine structures 7 arranged to form a grating (stripe) in a planar view. Further, in the example shown in FIGS. 4B-1 and 4B-2, the metal fine structure layer 6 has a structure in which there is included a plurality of metal fine structure arrays each having a plurality of metal fine structures 7 arranged side by side at a predetermined pitch in a predetermined direction in the planar view, and the metal fine structure arrays are arranged side by side at a predetermined pitch in a direction (an orthogonal direction) intersecting with the predetermined direction. In other words, in this example, the metal fine structure layer 6 has the metal fine structures 7 arranged in a matrix in the planar view.

In the case in which the metal fine structure layer 6 is formed of the metal fine structures 7 having the particulate or striped shape, the number of the metal fine structures 7 is only required to be two or more, and is preferably equal to or larger than 10, and more preferably equal to or larger than 100. It should be noted that although in the example shown in FIGS. 4A-1 to 4B-2, there are disposed the metal fine structures 7 having the same shape, it is also possible to dispose the metal fine structures 7 that are different in shape from each other, and for example, the metal fine structures 7 having the striped shape and the metal fine structures 7 having the particulate shape can be included in a mixed manner.

The metal fine structures 7 are each disposed separately from the metal layer 2 in the thickness direction due to the existence of the dielectric layer 4. The metal fine structures 7 are each disposed above the metal layer 2 via the dielectric layer 4. Although in the example shown in FIG. 3, the dielectric layer 4 is disposed above the metal layer 2, and the metal fine structures 7 are formed above the dielectric layer 4, the dielectric layer 4 is not limited to the layered shape providing the metal layer 2 and the metal fine structures 7 are disposed separately from each other in the thickness direction. Further, although not shown in the drawings, in the case of disposing the metal fine structures 7 above the dielectric layer 4, it is possible to make an adhesion layer intervene between the dielectric layer 4 and the metal fine structures 7. As the material of the adhesion layer, there can be cited gold, copper, aluminum, palladium, nickel, platinum, molybdenum, chromium, titanium, alloys or complexes of any of these materials, titanium oxide, tungsten oxide, and so on.

The shapes of the metal fine structures 7 are not particularly limited, and in the case of, for example, adopting the particulate structures, the shapes can be circular shapes, elliptical shapes, polygonal shapes, infinite shapes, or shapes obtained by combining these shapes in the case of projecting the metal fine structures 7 in the thickness direction of the metal layer 2 or the dielectric layer 4 (in the planar view from the thickness direction), and can also be circular shapes, elliptical shapes, polygonal shapes, infinite shapes, or shapes obtained by combining these shapes in the case of projecting the metal fine structures 7 in a direction perpendicular to the thickness direction of the metal layer 2 or the dielectric layer 4. Although in the example shown in FIG. 3, the metal fine structures 7 is drawn to have a columnar shape having a center axis along the thickness direction of the dielectric layer 4, the shape of each of the metal fine structures 7 is not limited to this example, but can be, for example, a prismatic shape, an elliptic cylindrical shape, a hemispherical shape, spherical shape, a pyramid shape, or a frustum shape.

The size T in the height direction (the thickness direction of the dielectric layer 4) of the metal fine structure 7 denotes the length of a zone in which the metal fine structure 7 can be cut by a plane perpendicular to the height direction, and can be set to be no smaller than 1 nm and no larger than 300 nm. Further, the size in a first direction perpendicular to the height direction of the metal fine structure 7 denotes the length of a zone in which the metal fine structure 7 can be cut by a plane perpendicular to the first direction, and can be set to be no smaller than 5 nm and no larger than 300 nm. In the case in which, for example, the shape of the metal fine structure 7 is a cylinder having a center axis along the height direction, the size (the height of the cylinder) in the height direction of the metal fine structure 7 can be set to be no smaller than 1 nm and no larger than 300 nm, preferably no smaller than 2 nm and no larger than 100 nm, more preferably no smaller than 3 nm and no larger than 50 nm, and further preferably no smaller than 4 nm and no larger than 40 nm. Further, in the case in which the shape of the metal fine structure 7 is a cylinder having the center axis along the height direction, the size (the diameter of the bottom surface of the cylinder) of the metal fine structure 7 can be set to be no smaller than 10 nm and no larger than 300 nm, preferably no smaller than 20 nm and no larger than 200 nm, more preferably no smaller than 25 nm and no larger than 180 nm.

The shape and the material of the metal fine structure 7 are arbitrary as long as the localized surface plasmon (LSP) can be generated due to the irradiation with the incident light (the excitation light). As the material capable of generating the localized surface plasmon due to the light in the vicinity of the visible range, there can be cited gold, silver, aluminum, copper, platinum, palladium, nickel, and alloys of any of these metals. Among these materials, Au and Ag are more preferable as the material of the metal fine structures 7. By selecting such a material, the LSP having higher intensity can be obtained, and the degree of the electrical field enhancement of the whole of the element can be enhanced.

The metal fine structures 7 can be formed using, for example, a method of forming a thin film using a sputtering process, an evaporation process, and so on and then performing patterning, a micro-contact printing method, or a nanoimprint method. Further, the metal fine structures 7 can be formed using, for example, a lithography method of exposing a resist, which is applied on the substrate, with an electron beam lithography or the like, depositing a metal thin film using a sputtering process, an evaporation process, or the like, and then removing the resist to thereby perform patterning. Further, the metal fine structures 7 can also be formed using a colloid chemical method, and can also be arranged on the dielectric layer 4 using an arbitrary method.

Further, the metal fine structures 7 can also be formed using an interference exposure method. Specifically, the exposure for forming the pattern can be performed using the interference pattern of the laser beam. Further, according to this method, multiple exposure and multiple beam exposure are possible, and the metal fine structures 7 having a periodic pattern can be formed with extreme ease. For example, in the case of forming a striped pattern, such a pattern can be formed by exposing the resist or the like to the interference pattern of the laser beam. Further, in the case of forming a pattern having a two-dimensional lattice shape, such a pattern can be formed by exposing the resist or the like to the interference pattern of the laser beam in an intersecting manner at the same time or in a batch manner. Such a method can make the device configuration small in scale compared to the electron beam lithography, and at the same time, can more efficiently manufacture a large number of sensor chips 10 on demand.

The metal fine structures 7 have a function of generating a localized surface plasmon (LSP) in the sensor chip 10 according to the present embodiment. By irradiating the metal fine structures 7 with the incident light (the excitation light) in a specific condition, the localized surface plasmon can be generated in the periphery of the metal fine structures 7. It is also possible to set the wavelength of the incident light (the excitation light), the thickness of the dielectric layer 4, the arrangement of the metal fine structures 7, and so on so that the localized surface plasmon generated in the metal fine structures 7 can interact with the propagating surface plasmon generated in the vicinity of the interface between the metal layer 2 and the dielectric layer 4.

The sensor chip 10 is irradiated with the incident light (the excitation light) from the metal fine structure layer 6 side. Then, the incident light (the excitation light) performs a variety of interactions such as diffraction, refraction, reflection, and so on with the metal fine structure layer 6, the dielectric layer 4, and the metal layer 2 to generate the plasmon resonance in the area irradiated with the incident light (the excitation light) and the vicinity of the area, and can thus exhibit the high electrical field enhancement effect.

In the sensor chip 10 hereinabove described as an example, an extremely large enhanced electrical field is formed in the vicinity of the metal fine structures 7 of the metal fine structure layer 6 by irradiation with the incident light (excitation light). Therefore, by irradiating the metal fine structures 7 of the metal fine structure layer 6 of the sensor chip 10 with the incident light (the excitation light) in the state in which the target substance is adsorbed (attached, contacted) to the metal fine structures 7, both of the incident light (the excitation light) and the Raman scattering light due to the target substance can be significantly amplified.

Further, such a sensor chip 10 is held by the holding body 20 of the sensor unit 50, and used for, for example, a Raman spectroscopic device as the sensor unit array 100 having the plurality of sensor units 50 connected to each other. In such a case, the sensor unit 50 and a flow channel of the sample are preferably disposed so that the target substance in the sample is easily adsorbed (attached, contacted) to the metal fine structures 7 of the metal fine structure layer 6 of the sensor chip 10.

1.1.2. Holding Body

The holding body 20 has a function of holding the sensor chip 10. The sensor unit array 100 includes the plurality of sensor units 50, and each of the sensor units 50 includes the holding body 20. Each of the plurality of holding bodies 20 can be disposed adjacently to other holding bodies 20. Further, in the case in which the two holding bodies 20 are disposed adjacently to each other, a housing chamber 22 partitioned by the two holding bodies 20 is formed. In this case, the housing chamber 22 houses the sensor chip 10 held by the holding body 20 of one of the sensor units 50.

As shown in FIGS. 1A, 1B, 2A, 2B, and 2C, the holding bodies 20 are disposed adjacently to each other to thereby make it possible to form the housing chamber 22. In the example shown in the drawing, the holding body 20 is formed of a base section 24, and a cylindrical section 26 integrally connected to the base section 24. Further, the base section 24 of one of the holding bodies 20 and the cylindrical section 26 of the other of the holding bodies 20 are made to be adjacent to each other so as to fit to each other, to thereby form the housing chamber 22 partitioned by the base section 24 of one of the holding bodies 20 and the cylindrical section 26 of the other of the holding bodies 20. Further, other holding bodies 20 are arranged side by side in a line adjacently to each other so as to extend in the direction in which such two holding bodies 20 are adjacent to each other, and thus, the sensor unit array 100 is formed.

FIGS. 1A, 1B, 2A, 2B, and 2C show only an example, and the shape of the holding body is not at all limited providing the function described above is provided. By providing the function described above, the sensor chip 10 can be protected from disturbances such as contact in at least handling by the user, keeping, and storing the sensor chip 10. Further, plural sensor units 50 are arranged adjacently to each other, and thus, even if the size of each of the sensor units 50 is small, it is possible to achieve the size easy to handle with a hand of the user.

It is more preferable for the shape of the holding body 20 to be a shape fitting into (engaging with, nesting with) the adjacent holding body 20. In other words, it is more preferable that when the two holding bodies 20 are disposed adjacently to each other, the two holding bodies 20 are connected (jointed) (fitted) to (engaged with) each other so that no gap exists between the two holding bodies 20. According to such a configuration, the airtightness of the housing chamber 22 thus formed can be improved, and thus the effect of inhibiting the moisture or the like from adsorbing to the sensor chip 10 can be enhanced. Further, the connection between the two holding bodies 20 can be more surely achieved, the housing chamber 22 can be maintained with an appropriate strength as the sensor unit array 100, and it is possible to make the two holding bodies 20 easy to separate with a hand of the user.

Figure 5:
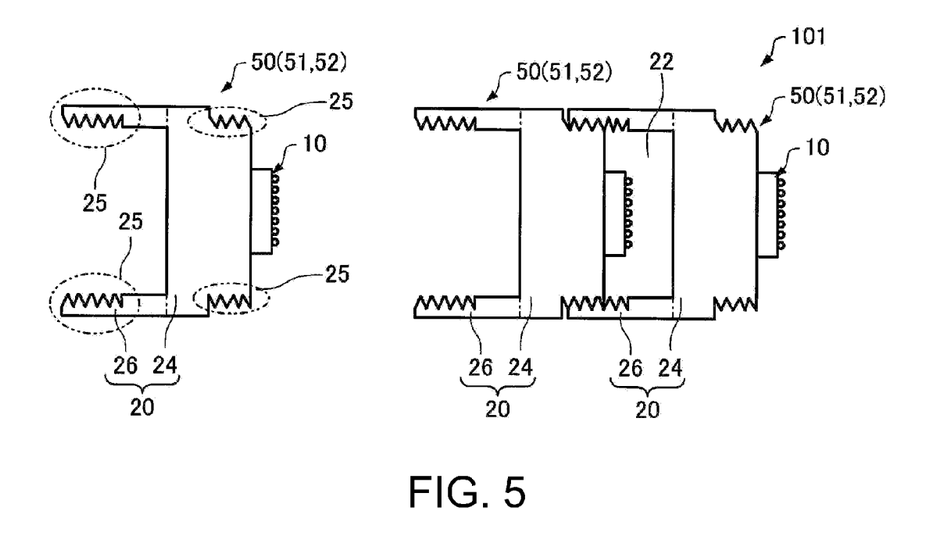
FIG. 5 is a schematic diagram of a cross-section of a sensor unit array according to a modified embodiment of the invention.
Figure 6:
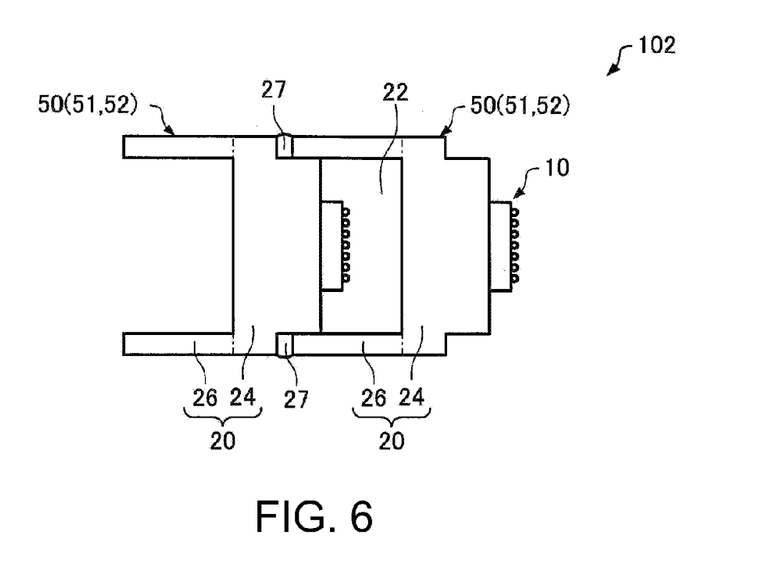
FIG. 6 is a schematic diagram of a cross-section of a sensor unit array according to a modified embodiment of the invention.

Further, from a similar viewpoint, for example, as shown in FIG. 5, the holding body 20 can have a shape capable of screwing together with the adjacent holding body 20. FIGS. 5 and 6 are diagrams schematically showing a sensor unit array 101 and a sensor unit array 102 according respectively to modified embodiments. Here, screwing denotes threaded connection with a screw structure 25, and the configuration of the screw thread and the screw pitch are not particularly limited. If the holding body 20 has the shape capable of screwing together with the adjacent holding body 20, the connection between the two holding bodies 20 can be more surely achieved, the housing chamber 22 can be maintained with an appropriate strength as the sensor unit array 101, and it is possible to make the two holding bodies 20 easy to separate with a hand of the user.

Further, for example, as shown in FIG. 6, the holding body 20 can also be bonded to the adjacent holding body 20 with an adhesive 27. The adhesive 27 is not particularly limited, and further, the position at which the adhesive 27 is disposed and the application method of the adhesive 27 are not at all limited. It is assumed that the adhesive 27 has an adhesion force allowing the user to separate the two holding bodies 20 from each other by hand. According to such a configuration as described above, the connection between the two holding bodies 20 can be more surely achieved, the housing chamber 22 can be maintained with an appropriate strength as the sensor unit array 102, and it is possible to make the two holding bodies 20 easy to separate with a hand of the user.

Further, although not shown in the drawing, the connection between the two holding bodies 20 can also be achieved including a member such as an arbitrary packing (gasket), or an O-ring. Further, the connection between the two holding bodies 20 can also be achieved arbitrarily including a mechanism (e.g., a pawl and a catch, a click-stop mechanism, and a cylinder for making the holding bodies 20 align inside the cylinder) for supporting the connection.

Incidentally, in the examples shown in FIGS. 1A, 1B, 2A, 2B, 2C, 5, and 6, the holding bodies 20 are all connected so that the base section 24 is located inside the cylindrical section 26 of the adjacent holding body 20. In other words focusing attention on the two sensor units 50 to be connected to each other, when the first sensor unit 51 and the second sensor unit 52 are disposed so as to be adjacent to each other in the sensor unit array 100, the base section 24 of the first sensor unit 51 is disposed so as to have contact with the inner surface of the cylindrical section 26 of the second sensor unit 52. Further, the sensor chip 10 is disposed in the base section 24 of the holding body 20 of the first sensor unit 51, and the housing chamber 22 is constituted by the base section 24 of the first sensor unit 51, the base section 24 of the second sensor unit 52, and the cylindrical section 26 of the second sensor unit 52.

By adopting such a configuration as described above, when separating the two holding bodies 20 from each other, it results that the sensor chip 10 is disposed in the tip portion of the sensor unit 50. Since the sensor chip 10 is disposed in the tip portion of the sensor unit 50, even in the case of forming the sensor unit array 100, it results that the sensor chip 10 is located in the tip portion of the sensor unit array 100. Thus, since a member of the sensor unit 50 for shielding the sensor chip 10 thus exposed from the lateral side can be eliminated, it is possible to make the fluid including the target substance easier to have contact with the sensor chip 10.

Although the sensor unit 50 according to the present embodiment has the base section 24 and the cylindrical section 26, the shapes of the base section 24 and the cylindrical section 26 are not limited to the shapes described above as an example. The base section 24 and the cylindrical section 26 can be integrated with each other, or can also be separate members. Further, although in the example described above, the base section 24 has a roughly disk-like shape, it is also possible for the base section 24 to have, for example, a polygonal shape in a planar view, or a concavo-convex shape viewed from a lateral side (in the case in which the base section 24 has a plate-like shape, the thickness of the plate can be partially different). Although the base section 24 is provided with the sensor chip 10, the position of the sensor chip 10 in the base section 24 is also not particularly limited. It should be noted that as described above, taking the structure of the cylindrical section 26 into consideration, it is preferable for the sensor chip 10 to be disposed at a position in the base section 24 where the sensor chip 10 is disposed in the tip portion of the sensor unit 50.

Although in the example described above, the cylindrical section 26 has a cylindrical shape, the shape of the cylindrical section 26 is not limited to the example, but the cross-sectional shape of the cylinder can also be, for example, a polygonal shape. Further, although in the example described above, the center axis of the cylindrical section 26 is arranged to be parallel to the thickness direction of the base section 24, the center axis can also be tilted. In other words, the cylindrical section 26 can have the rectangular shape viewed from the lateral side as in the example described above, or can have a parallelogram side surface. It should be noted that even in the case in which the center axis of the cylindrical section 26 is formed obliquely to the thickness direction of the base section 24, it is possible to realize the arrangement in which the member of the sensor unit 50 for shielding the sensor chip 10 from the lateral side is eliminated.

Further, although in the example described above, the holding body 20 is constituted by the base section 24 and the cylindrical section 26, it is also possible for the holding body 20 to be used as the substrate 1 or the metal layer 2 of the sensor chip 10. In the case in which the holding body 20 is also used as the substrate 1 or the metal layer 2 of the sensor chip 10, the sensor unit 50 can be regarded as a configuration having a base body and a sensor section provided to the base body. In other words, in this case, it results that the base body has substantially the same action and function as those of the holding body 20, and the sensor section has substantially the same action and function as those of the sensor chip 10. Therefore, in this case, in the present specification, assuming that the substrate 1 or the metal layer 2 is the base body, and the sensor section is provided to the base body, by replacing the sensor chip 10 with the sensor section, and replacing the holding body 20 with the base body, the explanation can be presented.

It should be noted that in other words focusing attention on the two sensor units 50 out of the plurality of sensor units 50, it can be said that in such a configuration, the first sensor unit 51 and the second sensor unit 52 each have the base body and the sensor section provided to the base body, in the case in which the first sensor unit 51 and the second sensor unit 52 are disposed adjacently to each other, the housing chamber 22 partitioned by the respective base bodies of the first sensor unit 51 and the second sensor unit 52 is formed, and the sensor section of either one of the first sensor unit 51 and the second sensor unit 52 is disposed inside the housing chamber 22.

The material of the holding body is not particularly limited, but an arbitrary material such as polymer, metal, or ceramics can be adopted. It should be noted that in the case of the configuration in which the holding body 20 is also used as the substrate 1 of the sensor chip 10, the holding body 20 can be formed of glass, silicon, polymer, or the like, and in the case of the configuration in which the holding body 20 is also used as the metal layer 2 of the sensor chip 10, silver, gold, aluminum, copper, platinum, or an alloy of any of these materials can be adopted as the material.

The sensor unit array 100 is constituted by the plurality of sensor units described above disposed adjacently to each other. Therefore, there is achieved a size easy to handle with a hand of the user even if the size of each of the sensor units 50 is small. Further, since in such a sensor unit array 100, the sensor chip 10 is disposed inside the housing chamber, when keeping or storing the sensor unit array 100, deterioration of the sensor chip 10 is inhibited, and thus, the characteristic of high sensitivity can be maintained. Further, since the sensor chip 10 can be protected from disturbances such as contact in handling by the user, keeping, and storing the sensor chip 10, the characteristic of high sensitivity can be maintained.

1.2. Housing Chamber

In the sensor unit array 100 according to the present embodiment, plural sensor units 50 described above are disposed adjacently to each other, and the housing chamber 22 is formed between the sensor units 50 adjacent to each other. The housing chamber 22 is opened by separating the two sensor units 50, which form the housing chamber 22, from each other, and then, the sensor chip 10 having been housed is exposed.

The shape, the capacity, and so on of the housing chamber 22 are not particularly limited. The capacity of the housing chamber 22 can be set to be, for example, no smaller than 20 $mm^3$ and no larger than 20000 $mm^3$, and preferably no smaller than 25 $mm^3$ and no larger than 3000 $mm^3$. The housing chamber 22 has a function of housing the sensor chip 10, inhibiting the ambient air from having contact with the sensor chip 10, and making it difficult for an external member and the ambient air to have contact with the sensor chip 10.

It is preferable for the housing chamber 22 to have an air-tight property. By enhancing the airtightness of the housing chamber 22, since the ambient air can be further inhibited from having contact with the sensor chip 10 housed therein, the shelf life of the sensor chip 10 can be improved.

An inert gas can be encapsulated in the housing chamber 22. The inert gas in this context denotes a gas not causing a conformational change of the sensor chip 10 even if the gas has contact with the sensor chip 10, a gas difficult to cause an adsorbed molecule, a gas including a molecule easily removed even if the molecule has once been adsorbed. As the specific inert gas, there can be cited a noble gas such as argon or neon, nitrogen, carbon dioxide, and so on, and air can also be adopted providing the air is sufficiently dried. If a water molecule adheres to the metal fine structures 7 of the sensor chip 10, the target substance is hindered from adhering (adsorbing) in some cases. Therefore, in the case in which the housing chamber 22 is sealed, the smaller the moisture amount in the housing chamber 22 is the better, and for example, the dew-point temperature in the housing chamber 22 is preferably 3° C. or lower. In the case of introducing the inert gas in the housing chamber 22, the dew-point temperature in the housing chamber 22 is preferably 3° C. or lower.

As a method of introducing the inert gas in the housing chamber 22, there can be cited a method of, for example, connecting (disposing adjacently) the plurality of sensor units 50 to each other in a glove box of the inert gas with the dew-point controlled. Thus, the housing chamber 22 with the inert gas encapsulated can be formed.

When the inert gas is encapsulated in the housing chamber 22, the deterioration of the sensor chip 10 is further suppressed in keeping and storing the sensor unit array 100, and thus, the characteristic of high sensitivity can be maintained for a longer period of time.

1.3. Arrangement of Sensor Chip

The sensor chip 10 is held by the holding body 20 to constitute the sensor unit 50. Further, in the case in which the plurality of sensor units 50 are disposed adjacently to each other to thereby constitute the sensor unit array 100, the sensor chips 10 other than the sensor chip 10 of the sensor unit 50 located at the end portion are housed in the housing chamber 22.

The position at which the sensor chip 10 is held is not particularly limited, but it is preferable to hold the sensor chip 10 at a position where the sensor chip 10 is not shielded by a member (e.g., the holding body 20) of the sensor unit 50 in the case of viewing one of the sensor units 50. In other words, it is preferable that the metal fine structure layer 6 of the sensor chip 10 is disposed in the end portion of the sensor unit 50, and is held so that an imaginary plane including the plane in which the metal fine structure layer 6 is formed does not cut the sensor unit 50.

If the sensor chip 10 is held in such a manner as described above, since a member of the sensor unit 50 for shielding the sensor chip 10 from the lateral side is eliminated, it is possible to make the fluid including the target substance easily contact with the sensor chip 10 from the lateral side.

In the sensor unit 50 according to the present embodiment, since the sensor chip 10 is disposed in the tip portion of the sensor unit 50, by removing the sensor unit 50 located at the tip of the sensor unit array 100 and having the sensor chip 10 exposed, it results that the sensor chip 10 of the adjacent sensor unit 50 is sequentially positioned at the tip portion of the sensor unit array 100. Thus, since a member of the sensor unit 50 for shielding the sensor chip 10 thus exposed from the side surface can be eliminated, it is possible to make the fluid including the target substance easier to have contact with the sensor chip 10.

1.4. Other Constituents 1.4.1. Rotation Restricting Mechanism

The sensor unit array 100 according to the present embodiment can include a rotation restricting mechanism 28 (see FIGS. 2A to 2C) provided to the holding body 20 of the sensor unit 50. The rotation restricting mechanism 28 has a function of restricting the sensor units 50 adjacent to each other from rotating relatively to each other around an axis along the direction in which the sensor units 50 are arranged. In other words focusing attention on the two sensor units 50 adjacent to each other, the holding body 20 can have the rotation restricting mechanism 28 for restricting the first sensor unit 51 and the second sensor unit 52 from rotating relatively to each other around the axis along the direction in which the first sensor unit 51 and the second sensor unit 52 are arranged when the first sensor unit 51 and the second sensor unit 52 are disposed adjacently to each other.

The rotation restricting mechanism 28 can be arbitrarily configured as long as the function described above is provided. In the example shown in FIGS. 2A through 2C, the rotation restricting mechanism 28 has a shape (a chord-arc shape) obtained by cutting a part of a circle with a chord provided to both of the base section 24 and the cylindrical section 26 in the case of the planar view of the base section 24 and the cylindrical section 26. According to such a rotation restricting mechanism 28, the angle at which the two holding bodies 20 can be connected is restricted in the case of disposing the two holding bodies 20 adjacently to each other, and thus, it is possible to make the angles of the sensor chips 10 uniform, which are held by the two holding bodies 20, around the axis along the direction in which the sensor units 50 adjacent to each other are arranged.

Further, the rotation restricting mechanism 28 can also function as a guide (key) used when mounting the sensor unit array 100 to the Raman spectroscopic device or the like. In other words, it is also possible to provide a function of restricting the angle of the sensor unit array 100 around the axis along the longitudinal direction of the sensor unit array 100 when mounting the sensor unit array 100 to the mounting section of the Raman spectroscopic device or the like.

The rotation restricting mechanism 28 is not limited to the mechanism using the chord-arc shape, but there can also be adopted a mechanism including, for example, a projecting section (a projection shaped like a tab) projecting toward the outside of the cylindrical section 26, a groove or a cutout provided to the cylindrical section 26, or a combination of these constituents although not shown in the drawings. Further, it is also possible for the rotation restricting mechanism 28 to be arranged to be able to dispose the two sensor units 50 adjacently to each other at a predetermined angle by, for example, providing the color to the cylindrical section 26 to make it easy for the user or the assembling operator to adjust the angle besides the function of structurally restricting the angle. It should be noted that in the case of adopting the configuration in which the two sensor units 50 are screwed together with each other, a projection for restricting the rotation, a mark for adjusting the rotational position, and so on can be arbitrarily adopted as the rotation restricting mechanism 28.

In the case in which the holding body 20 has the rotation restricting mechanism 28, when forming the sensor unit array 100, it is possible to make the angles of the respective sensor chips 10 uniform around the axis along the direction in which the first sensor unit 51 and the second sensor unit 52 are arranged. Thus, in the case of, for example, mounting the sensor unit array 100 to the Raman spectroscopic device, it is possible to stably set the incident angle of the excitation light from the light source to the sensor chip 10, and the rotational angle of the sensor chip 10 with respect to the light source to predetermined angles in each of the sensor units 50. Further, in the case in which, for example, the excitation light is polarized light, and in the case in which the arrangement of the metal fine structures of the sensor chip has an anisotropic nature, the sensor chip can be appropriately arranged at a predetermined angle. Thus, in the case of mounting such a sensor unit array 100 to the Raman spectroscopic device, the adjustment operation for appropriately mounting the sensor unit array 100 becomes extremely easy, and it is possible to further simplify the handling of the sensor unit array 100, namely the sensor chip 10.

1.4.2. Cap

The sensor unit array 100 according to the present embodiment can include a cap. The cap can be put over the sensor unit 50 at the end on the side where the sensor chip 10 is exposed among the sensor units 50 constituting the sensor unit array 100. It is possible for the cap to have the same structure as that of the holding body 20 constituting the sensor unit 50. Specifically, the cap can be obtained by removing the sensor chip 10 from the sensor unit 50 described above. In the case in which the cap has the same structure as that of the holding body 20, the cap is removed from the one end, and then the cap can be mounted on the other end. Since the sensor unit array 100 has the cap, the sensor chip 10 can be prevented from being exposed, and thus, it is possible to stably keep and transport the sensor unit array 100.

1.5. Handling of Sensor Unit Array

Figure 7A:
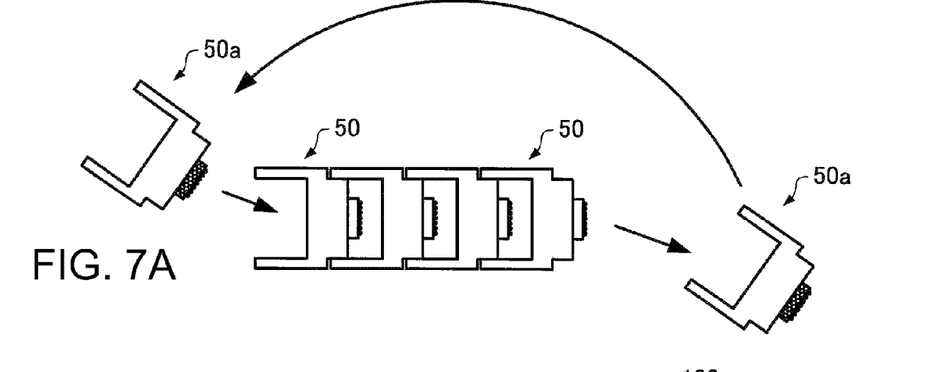
FIGS. 7A through 7C are each a schematic diagram showing handling of the sensor unit array according to the embodiment.
Figure 7B:
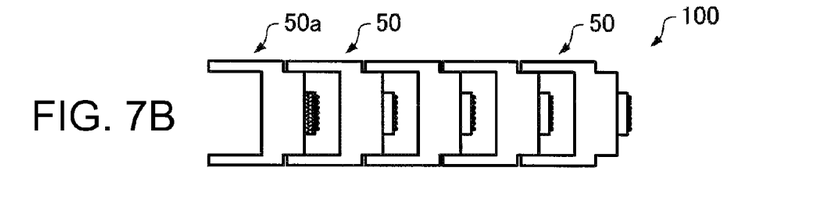
Figure 7C:
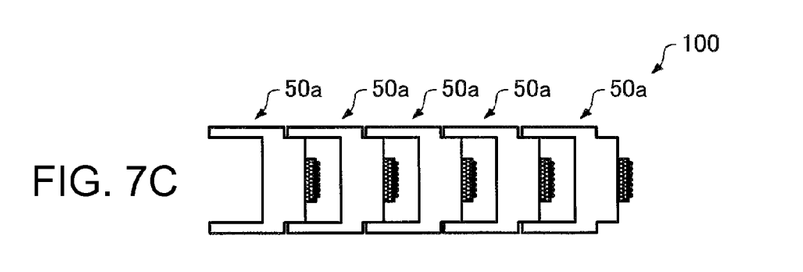

As shown in FIGS. 1A and 1B, the sensor unit array 100 is formed of a plurality of sensor units 50, and the sensor units 50 are arranged side by side in a straight line. FIGS. 7A through 7C are diagrams schematically showing the handling of the sensor unit array 100. In the example shown in FIGS. 1A and 1B, the sensor unit array 100 is composed of the five sensor units 50, and the sensor chip 10 of the sensor unit 50 located at one end is exposed. In the case in which the sensor chip 10 exposed has been used for an analysis or the like, and has become a used sensor chip, it is necessary to expose a new sensor chip 10 on the one end of the sensor unit array 100.

In the sensor unit array 100 according to the present embodiment, by separating either part of the sensor units 50 connected to each other, the new sensor chip 10 can be exposed. Further, it is also possible to expose the new sensor chip 10 by separating the sensor unit 50 (located at the one end in the present example) in which the used sensor chip 10 is held. Therefore, according to the sensor unit array 100 of the present embodiment, even if the size of each of the sensor units 50 is small, it is possible to easily set the new sensor chip 10 to available state by the hand of the user.

Further, FIGS. 7A through 7C are each a schematic diagram showing the handling of the sensor unit array 100 according to the present embodiment. By constituting the sensor unit array 100 according to the present embodiment from the plurality of sensor units 50 having the same shape, the used sensor unit 50a, which has been located at the one end and then removed, can be sequentially disposed on the other end adjacently to each other as shown in FIG. 7A (see FIGS. 7B and 7C). Thus, since the size (dimension) of the sensor unit array 100 can be maintained even in the case of exposing the new sensor chip 10, the easiness of handling can be appropriately maintained.

Figure 8:
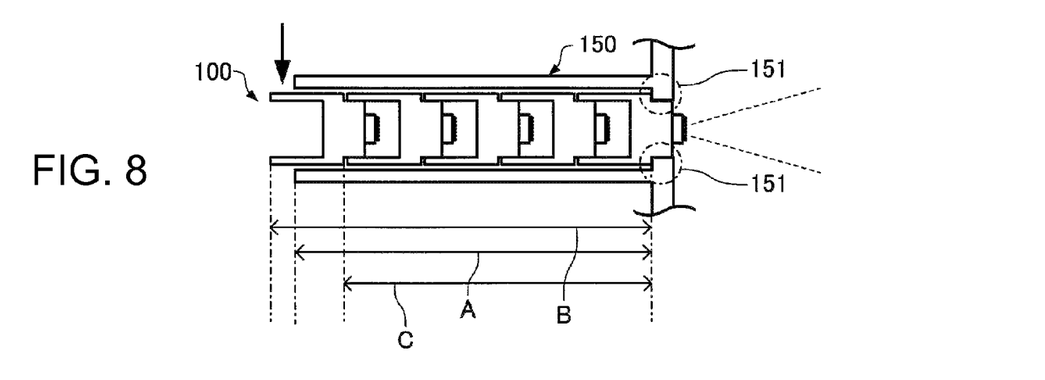
FIG. 8 is a diagram schematically showing a relationship between the sensor unit array according to the embodiment and a mounting section.

FIG. 8 is a diagram schematically showing a relationship between the sensor unit array 100 according to the embodiment and a mounting section 150 of an analysis device or the like. In the case of mounting the sensor unit array 100 to the mounting section 150 (in the configuration of mounting the sensor unit array 100 by inserting the sensor unit array 100 with the sensor chip 10 located on the tip side) of the Raman spectroscopic device described later or the like and then using the sensor unit array 100, it is possible to adopt a configuration in which at least a part of the sensor unit 50 located on the back end side projects from the mounting section 150 (see the arrow in the drawing) in the mounting state (the state in which the sensor chip 10 is disposed in place where the sensor chip 10 is used for the measurement).

In other words, in the mounting state, it is possible to set the depth (the length A to the end (the position determined by a positioning mechanism 151) in the insertion direction) of the mounting section 150 to be shorter than the length (the length B from the back end of the sensor unit array 100 to the end (the position determined by the positioning mechanism 151) in the direction in which the sensor units 50 are arranged) of the sensor unit array 100, and longer than the length (the length C to the end (the position determined by the positioning mechanism 151) in the direction in which the sensor units 50 are arranged) of the sensor unit array 100 with one of the sensor units 50 removed. It should be noted that in the example shown in the drawing, the positioning mechanism 151 has a shape of fitting in a part of the base section 24 of the sensor unit 50.

According to such a configuration as described above, when removing the sensor unit 50 on the tip side, the new sensor chip 10 cannot be disposed at a predetermined position unless the sensor unit 50 is connected on the back end side, and further, it is possible to make it difficult to draw (pull out) the sensor unit array 100 from the mounting section. Therefore, it is possible for the user to use the sensor unit 50 including the used sensor chip 10 as a jig to be connected on the back end side for disposing the new sensor chip 10 at the predetermined position, and at the same time drawing (pulling out) the sensor unit array 100 from the mounting section without scrapping the sensor unit 50 including the used sensor chip 10. Further, the user cannot continue to use the sensor unit array 100 unless such an operation as described above is performed. Therefore, it is possible to arrange that the used sensor units 50a are used without being scrapped until all of the sensor units 50 included in the sensor unit array 100 are changed to the used sensor units 50a (see FIG. 7C).

Thus, the handling of the case of scrapping the sensor unit array 100 (FIG. 7C), in which all of the sensor units 50 included have been changed to the used sensor units 50a, is made easier. Further, according to this configuration, it is also possible to easily perform collection of the used sensor unit array 100 at stores or the like. Further, according to such a process as described above, the noble metal included in the sensor chip 10, the holding body 20 constituting the sensor unit 50, the material of these constituents, and so on are prevented from being scrapped during the use of the sensor unit array 100. Therefore, by collecting the used sensor unit array 100 at stores or the like, environmental contamination or the like can be suppressed, and at the same time, the resources such as the noble metal can be collected and then recycled with efficiency at high density. It should be noted that the same can be applied to the case of including the cap described above, and the cap can be used as the jig, and then collected after use.

2. Raman Spectroscopic Device

The Raman spectroscopic device according to the present embodiment is provided with the sensor unit array described above, a light source, and a detector.

Figure 9:
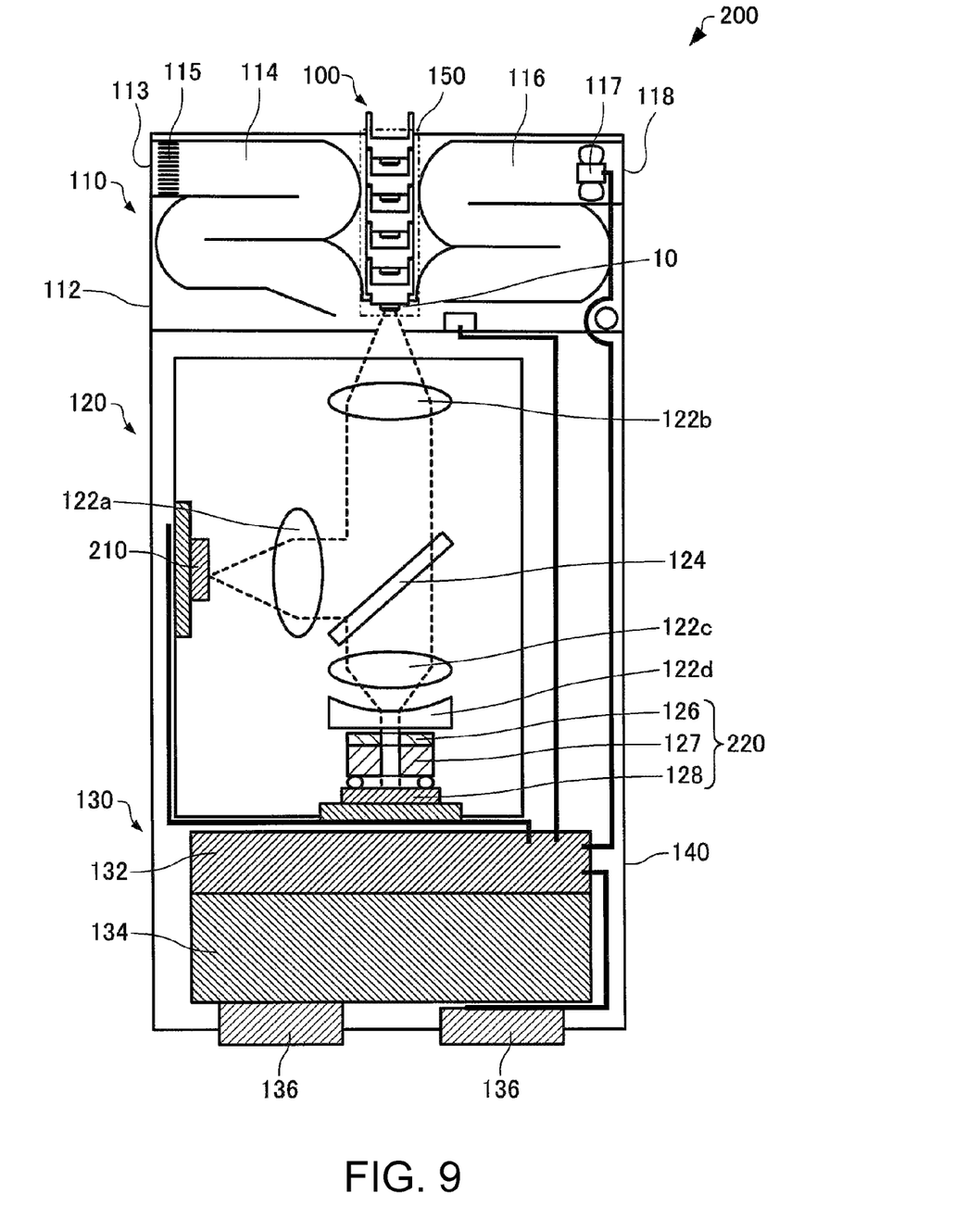
FIG. 9 is a schematic diagram of a Raman spectroscopic device according to an embodiment of the invention.

FIG. 9 is a diagram schematically showing the Raman spectroscopic device 200 according to the present embodiment. The Raman spectroscopic device 200 is for detecting the Raman scattering light from the target substance to perform an analysis (a qualitative analysis, a quantitative analysis), and includes a light source 210, a gas sample holding section 110, a detection section 120, a control section 130, and a housing 140 for housing the detection section 120 and the control section 130 as shown in FIG. 9. The gas sample holding section 110 includes the sensor unit array according to the invention. Hereinafter, an example including the sensor unit array 100 described above will be explained.

The gas sample holding section 110 includes the sensor unit array 100, a cover 112 provided with the mounting section 150 to which the sensor unit array 100 is mounted, a suction channel 114, and an exhaust channel 116.

The mounting section 150 can mount the sensor unit array 100, and has a shape with which the sensor chip 10 of the sensor unit 50 located on the one end of the sensor unit array 100 can be disposed at a position to be irradiated with the excitation light. In the present embodiment, the mounting section 150 has a structure of mounting the sensor unit array 100 by inserting the sensor unit array 100 from the side on which the sensor chip 10 is exposed. Although not shown in the drawing, it is also possible for the mounting section 150 to include a mechanism for stably fixing the sensor unit array 100, a mechanism for preventing the sensor unit array 100 from rotating around the center axis, a mechanism for limiting the angle around the center axis to a predetermined angle, and so on.

The detection section 120 includes a light source 210, lenses 122a, 122b, 122c, and 122d, a half mirror 124, and a photodetector 220. The control section 130 includes a detection control section 132 for processing a signal detected in the photodetector 220 to control the photodetector 220, and a power control section 134 for controlling electric power and a voltage of the light source 210 and so on. As shown in FIG. 9, the control section 130 can be electrically connected to connection sections 136 for achieving connection to an external device.

In the Raman spectroscopic device 200, when a suction mechanism 117 provided to the exhaust channel 116 is operated, a negative pressure is applied in the suction channel 114 and the exhaust channel 116, and the gas sample including the target substance to be the detection object is suctioned through a suction port 113. The suction port 113 is provided with a dust filter 115, and relatively large dust, some water vapor, and so on can be removed. The gas sample passes through the suction channel 114 and the exhaust channel 116, and is then discharged through the discharge port 118. The gas sample has contact with the metal fine structures 7 of the sensor chip 10 disposed in the tip portion of the sensor unit array 100 when passing through the channel.

The shapes of the suction channel 114 and the exhaust channel 116 are shapes for preventing the external light from entering the sensor unit array 100. Thus, since light other than the Raman scattering light and acting as noise is prevented from entering, the S/N ratio of the signal can be improved. The material constituting the channels 114, 116 is, for example, a material difficult to reflect light, or has a color difficult to reflect light.

The shapes of the suction channel 114 and the exhaust channel 116 are shapes for decreasing the fluid resistance with respect to the gas sample. Thus, the detection at high sensitivity becomes possible. For example, by changing the shapes of the channels 114, 116 to the smooth shapes by eliminating the corners as much as possible, retention of the gas sample in the corner sections can be eliminated. As the suction mechanism 117, there is used, for example, a fan motor or a pump having static pressure and air volume corresponding to the channel resistance.

In the Raman spectroscopic device 200, the light source 210 irradiates the sensor unit array 100 with the excitation light. The light source 210 is disposed so as to be able to emit linearly polarized light or circularly polarized light. Although not shown in the drawing, it is also possible to arrange that the incident angle θ of the excitation light emitted from the light source 210 can be arbitrarily changed in accordance with the excitation condition of the surface plasmon of the sensor unit array 100. The light source 210 can also be installed in a goniometer not shown or the like.

As an example of the light source 210, there can be cited a semiconductor laser, a gas laser, a halogen lamp, a high-pressure mercury lamp, a xenon lamp, and so on arbitrarily provided with a wavelength selective element, a filter, a polarizer, and so on.

The light emitted from the light source 210 is collected by the lens 122a, and then enters the sensor chip 10 of the sensor unit array 100 via the half mirror 124 and the lens 122b. The SERS light is emitted from the sensor chip 10, and the SERS light reaches the photodetector 220 via the lens 122b, the half mirror 124, and the lenses 122c, 122d. Therefore, the photodetector 220 detects the light emitted from the sensor chip 10. The Raman spectroscopic device 200 can be formed of a scattering spectroscopy system or a reflection spectroscopy system. Since the SERS light includes the Rayleigh scattering light having the same wavelength as the wavelength of the incident light from the light source 210, it is also possible to remove the Rayleigh scattering light using a filter 126 of the photodetector 220. The light from which the Rayleigh scattering light has been removed is received by a light receiving element 128 as the Raman scattering light via a spectroscope 127 of the photodetector 220. As the light receiving element 128, a photo diode, for example, is used.

The spectroscope 127 of the photodetector 220 is formed of, for example, an etalon using the Fabry-Perot resonance, and can be made to have a variable pass frequency band. The Raman spectrum unique to the target substance can be obtained by the light receiving element 128 of the photodetector 220, and the Raman spectrum thus obtained and the data held previously are compared with each other for matching to thereby make it possible to detect the signal intensity of the target substance.

It should be noted that the Raman spectroscopic device 200 is not limited to the example described above providing the Raman spectroscopic device includes the sensor unit array 100, the light source 210, and the photodetector 220, and is capable of adsorbing the target substance to the sensor chip 10 of the sensor unit array 100 and obtaining the Raman scattering light.

Further, in the case of detecting the Rayleigh scattering light as in a Raman spectroscopy method according to the present embodiment described above, it is also possible for the Raman spectroscopic device 200 to separate the Rayleigh scattering light and the Raman scattering light using the spectroscope without including the filter 126.

According to such a Raman spectroscopic device 200, since the sensor unit array 100 is mounted, the handling of the device is easy. Further, since the sensor chip 10 is disposed inside the housing chamber 22, the sensor chip 10 can be easily replaced.

3. Electronic Apparatus

Figure 10:
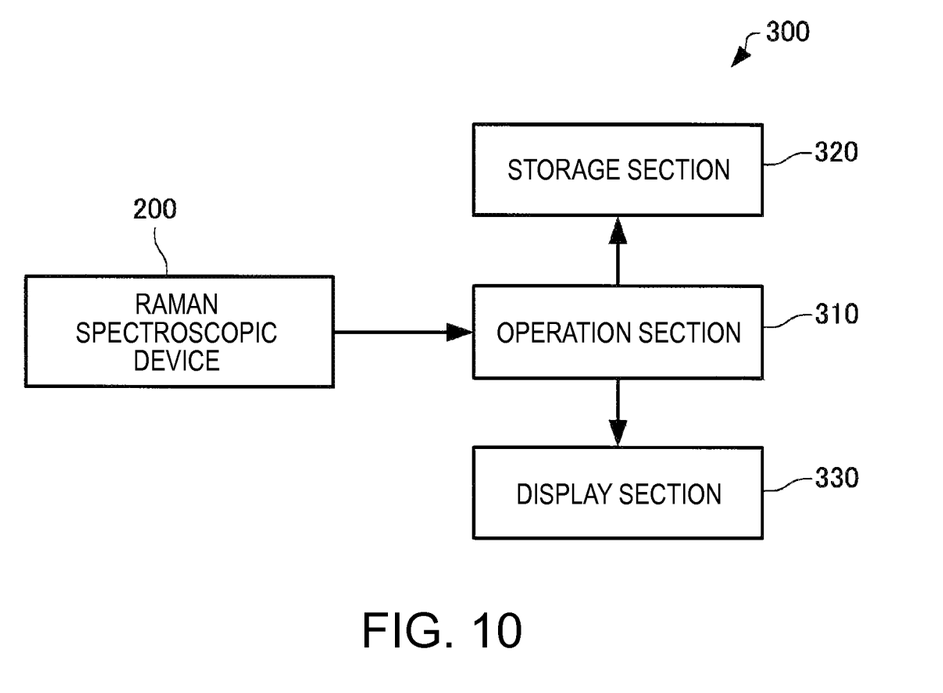
FIG. 10 is a schematic diagram of an electronic apparatus according to an embodiment of the invention.

Then, an electronic apparatus 300 according to the present embodiment will be explained with reference to the accompanying drawings. FIG. 10 is a diagram schematically showing the electronic apparatus 300 according to the present embodiment. The electronic apparatus 300 can include the Raman spectroscopic device according to the invention. Hereinafter, an example including the Raman spectroscopic device 200 described above will be explained.

As shown in FIG. 10, the electronic apparatus 300 includes the Raman spectroscopic device 200, an operation section 310 for performing an operation on health medical information based on the detection information from the photodetector 220, a storage section 320 for storing the health medical information, and a display section 330 for displaying the health medical information.

The operation section 310 is, for example, a personal computer or a personal digital assistance (PDA), and receives the detection information (e.g., a signal) transmitted from the photodetector 220. The operation section 310 performs the operation on the health medical information based on the detection information from the photodetector 220. The health medical information on which the operation has been performed is stored in the storage section 320.

The storage section 320 is, for example, a semiconductor memory or a hard disk drive, and can also be configured integrally with the operation section 310. The health medical information stored in the storage section 320 is transmitted to the display section 330.

The display section 330 is constituted by, for example, a display panel (e.g., a liquid crystal monitor), a printer, a light emitting body, and a speaker. The display section 330 displays or issues a notification based on, for example, the health medical information on which the operation has been performed by the operation section 310 so that the user can recognize the content of the information.

As the health medical information, there can be included information related to presence or absence or an amount of at least one biologically-relevant substance selected from a group consisting of bacteria, a virus, a protein, a nucleic acid, and an antigen/antibody, or at least one compound selected from an inorganic molecule and an organic molecule.

The electronic apparatus 300 includes the Raman spectroscopic device 200 described above. Therefore, in the electronic apparatus 300, the detection of a trace substance can be efficiently achieved at high sensitivity, and thus, the accurate health medical information can be provided.

For example, the electrical field enhancement element according to the invention can also be used as an affinity sensor for detecting presence or absence of adsorption of a substance such as presence or absence of adsorption of an antigen in an antigen-antibody reaction. By inputting white light to the affinity sensor, then the wavelength spectrum is measured by the spectroscope, and then detecting the shift amount of the surface plasmon resonance wavelength due to the adsorption, the affinity sensor can detect the absorption of the detection substance to the sensor chip at high sensitivity.

The invention is not limited to the embodiment described above, but can be further variously modified. For example, the invention includes configurations (e.g., configurations having the same function, the same way, and the same result, or configurations having the same object and the same advantage) substantially the same as the configuration described as the embodiment. Further, the invention includes configurations obtained by replacing a non-essential part of the configuration explained in the above description of the embodiment. Further, the invention includes configurations providing the same functions and the same advantage, or configurations capable of achieving the same object, as the configuration explained in the description of the embodiment. Further, the invention includes configurations obtained by adding a known technology to the configuration explained in the description of the embodiment.

The entire disclosure of Japanese Patent Application No. 2014-012556 filed Jan. 27, 2014 is expressly incorporated by reference herein.

What is claimed is:

1. A sensor unit array comprising:
   a first sensor unit including:
      a first sensor chip and a first holding body adapted to hold the first sensor chip; and
   a second sensor unit including:
      a second sensor chip and a second holding body adapted to hold the second sensor chip,
   wherein the first and second holding bodies are selectively disposed adjacent to one another to provide a housing chamber,
   the first sensor chip is disposed in the housing chamber, and
   at least one of the first and second holding bodies includes a rotation restricting mechanism adapted to restrict the first sensor unit and the second sensor unit from rotating relative to each other around an axis extending a direction in which the first sensor unit and the second sensor unit are arranged when the first sensor unit and the second sensor unit are adjacent to each other.

2. The sensor unit array according to claim 1, wherein the first holding body includes:
   a first base; and
   a first cylindrical wall projecting from the first base, the first sensor chip being provided to the first base;
   the second holding body includes:
   a second base; and
   a second cylindrical wall projecting from the second base, the second sensor chip being provided to the second base;
   the first sensor chip is housed in the housing chamber, and
   the housing chamber is formed with the first base, the second base and the second cylindrical wall.

3. The sensor unit array according to claim 2, wherein the first base is engaged with a surface of the second cylindrical wall when the first sensor unit and the second sensor unit are disposed adjacent to each other.

4. A Raman spectroscopic device comprising:
   a mounting section adapted to mount the sensor unit array according to claim 3;
   a light source adapted to irradiate the sensor unit array with excitation light; and
   a detector adapted to detect light emitted from the sensor unit array.

5. An electronic apparatus comprising:
   the Raman spectroscopic device according to claim 4;

an operation section adapted to perform an operation on select information based on detection information from the detector;
a storage section adapted to store the select information; and
a display section adapted to display the select information.

6. The sensor unit array according to claim 2, wherein the first base is bonded to a surface of the second cylindrical wall when the first sensor unit and the second sensor unit are disposed adjacent to each other.

7. A Raman spectroscopic device comprising:
a mounting section adapted to mount the sensor unit array according to claim 6;
a light source adapted to irradiate the sensor unit array with excitation light; and
a detector adapted to detect light emitted from the sensor unit array.

8. An electronic apparatus comprising:
the Raman spectroscopic device according to claim 7;
an operation section adapted to perform an operation on select information based on detection information from the detector;
a storage section adapted to store the select information; and
a display section adapted to display the select information.

9. The sensor unit array according to claim 2, wherein the first base threadingly engages a surface of the second cylindrical wall when the first sensor unit and the second sensor unit are disposed adjacent to each other.

10. A Raman spectroscopic device comprising:
a mounting section adapted to mount the sensor unit array according to claim 9;
a light source adapted to irradiate the sensor unit array with excitation light; and
a detector adapted to detect light emitted from the sensor unit array.

11. An electronic apparatus comprising:
the Raman spectroscopic device according to claim 10;
an operation section adapted to perform an operation on select information based on detection information from the detector;
a storage section adapted to store the select information; and
a display section adapted to display the select information.

12. A Raman spectroscopic device comprising:
a mounting section adapted to mount the sensor unit array according to claim 2;
a light source adapted to irradiate the sensor unit array with excitation light; and
a detector adapted to detect light emitted from the sensor unit array.

13. An electronic apparatus comprising:
the Raman spectroscopic device according to claim 12;
an operation section adapted to perform an operation on select information based on detection information from the detector;
a storage section adapted to store the select information; and
a display section adapted to display the select information.

14. The sensor unit array according to claim 1, wherein an inert gas is encapsulated in the housing chamber.

15. A Raman spectroscopic device comprising:
a mounting section adapted to mount the sensor unit array according to claim 1;
a light source adapted to irradiate the sensor unit array with excitation light; and
a detector adapted to detect light emitted from the sensor unit array.

16. An electronic apparatus comprising:
the Raman spectroscopic device according to claim 15;
an operation section adapted to perform an operation on select information based on detection information from the detector;
a storage section adapted to store the select information; and
a display section adapted to display the select information.

17. A sensor unit array comprising:
a first sensor unit having a first sensor and a first base body, the first sensor being provided on the first base body;
a second sensor unit having a second sensor and a second base body, the second sensor being provided on the second base body; and
a housing chamber that is provided by the first and second base bodies,
wherein
one of the first sensor and the second sensor is disposed in the housing chamber, and
at least one of the first and second base bodies includes a rotation restricting mechanism adapted to restrict the first sensor unit and the second sensor unit from rotating relative to each other around an axis extending in a direction in which the first sensor unit and the second sensor unit are arranged when the first sensor unit and the second sensor unit are adjacent to each other.

* * * * *